United States Patent [19]

Andoh et al.

[11] 4,246,427
[45] Jan. 20, 1981

[54] PROCESS FOR PRODUCING METHACRYLIC ACID

[75] Inventors: Naoki Andoh; Ituo Nishiwaki; Akira Iio; Masatoshi Arakawa, all of Yokkaichi, Japan

[73] Assignee: Japan Synthetic Rubber Co., Ltd., Tokyo, Japan

[21] Appl. No.: 966,999

[22] Filed: Dec. 6, 1978

Related U.S. Application Data

[63] Continuation of Ser. No. 728,678, Oct. 1, 1976, abandoned.

[30] Foreign Application Priority Data

Oct. 8, 1975 [JP] Japan ................... 50-120668

[51] Int. Cl.$^3$ .................... C07C 51/25; C07C 57/055
[52] U.S. Cl. .................... 562/535; 252/435; 252/437; 562/536
[58] Field of Search ............ 562/535; 252/435, 437

[56] References Cited

U.S. PATENT DOCUMENTS

| | | | |
|---|---|---|---|
| 3,875,220 | 4/1975 | White et al. | 562/535 |
| 3,998,877 | 12/1976 | Oda et al. | 562/535 |
| 4,180,678 | 12/1979 | Wada et al. | 562/535 |

FOREIGN PATENT DOCUMENTS 2514232 10/1975 Fed. Rep. of Germany ......... 562/535

*Primary Examiner*—Vivian Garner
*Attorney, Agent, or Firm*—Ladas & Parry

[57] ABSTRACT

Methacrylic acid is produced from methacrolein by gaseous phase oxidation in a very high selectivity, when methacrolein, molecular oxygen-containing gas and steam in a molar ratio of methacrolein:molecular oxygen:steam of 1:1–3:0–50 are subjected to reaction at a temperature in the range of 250° to 400° C., at a space velocity of 250 to 3,000 hr$^{-1}$ (at 0° C. and 1 atm.) with a novel catalyst having the following composition formula in atomic ratio:

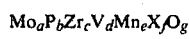

$$Mo_a P_b Zr_c V_d Mn_e X_f O_g$$

wherein X represents at least one member selected from the group consisting of potassium, rubidium, cesium and thallium, and a, b, c, d, e, f or g represents the number of atoms of Mo, P, Zr, V, Mn, X or O, respectively, and when a is 12, b is 0.5 to 5, c is 0.1 to 5, d is 0.05 to 3, e is 0.05 to 1.5, f is 0.1 to 3 and g is 40 to 60; and g is a number sufficient enough to satisfy the valencies of the respective catalyst component elements. Said catalyst has a high catalyst activity and a physical strength high enough for the catalyst to stand the severe conditions required for use on a commercial scale.

9 Claims, No Drawings

PROCESS FOR PRODUCING METHACRYLIC ACID

This is a continuation of application Ser. No. 728,678, filed Oct. 1, 1976, abandoned.

This invention relates to a process for producing methacrylic acid by gas-phase catalytic oxidation of methacrolein with a catalyst of a specific composition.

Various catalytic systems have heretofore been proposed for the production of methacrylic acid by gas-phase catalytic oxidation of methacrolein. However, these catalysts have merits and demerits and are not always satisfactory for the industrial application because of one or more defects such as low catalytic activity; short catalyst life inspite of a high initial conversion; deficient physical strengths such as insufficient resistance to impact or abrasion during the catalyst loading or during the reaction: and poor reproducibility in most cases.

For instance, most of the catalysts comprising phosphorus and molybdenum as major components are of short life, while when molybdenum-vanadium system catalysts are used, considerably large amounts of carbon oxides such as carbon monoxide and dioxide are formed and the necessary selectivity cannot be obtained.

Recent efforts for the improvement of catalysts for producing methacrylic acid have been directed mainly to the phosphorus-molybdenum-system catalysts. According to the experimental results obtained by the present inventors, the addition of zirconium to a phosphorus-molybdenum binary system results in an increase of conversion and selectivity, and particularly, the increase of selectivity is remarkable; and the addition of an alkali metal stabilizes the catalyst activity, improves the reproducibility, and prolongs the catalyst life. The addition of vanadium serves to increase the selectivity and, hence, to enhance the yield (Japanese Patent Application Kokai (laid-open) No. 70,318/75 (Plasdoc No. 61305 W)). From the above experimental results, it is considered that the phosphorus-molybdenum-zirconium-alkali-vanadium system Japanese Patent Application Kokai (laid-open) No. 70,318/75) gives a high yield of methacrylic acid and is a considerably improved catalyst for the production of methacrylic acid, as compared with a phosphorus-molybdenum-alkali-vanadium system (DT-OS No. 2,454,587).

However, these catalyst systems are not yet sufficient enough for the commercial scale production. A high selectivity is required in the oxidation of, for example, methacrolein to methacrylic acid and catalysts of the same composition manifest markedly different performance characteristics depending on the method of preparing the catalyst. In preparing the catalyst, basically a compound metal oxide is formed as the catalyst active component, the physical state of which markedly affects the conversion of methacrolein and the selectivity for methacrylic acid. Examples of the catalysts of various physical forms include a catalyst consisting of the catalyst active component as produced; a catalyst obtained by tabletting the catalyst active component admixed with a diluent; a catalyst consisting of the catalyst active component particles having a suitable particle size obtained by suitable seiving; and a catalyst prepared by adding a commercially available alumina or silicon carbide carrier to the molded catalyst active component. According to the results of experiments conducted by the present inventors, a catalyst prepared by the application of pressure, such as tabletting is generally inferior in performance to a catalyst prepared without applying pressure (for example, a catalyst prepared by simple crushing and seiving). Accordingly, the pore volume of the catalyst seems to contribute to the selectivity of the reaction. On the other hand, in order for a catalyst to be usable on a commercial scale, the catalyst should have a sufficient mechanical strength to resist disintegration during filling and reaction; when used in a fixed bed, the catalyst must not cause too large a pressure drop in gas flow. For these reasons, it is evident that a catalyst obtained by simple crushing and seiving of the catalyst active component is unsuitable for use on a commercial scale. Therefore, in order to estimate the performance of a catalyst prepared so as to acquire the necessary strength for use in the commercial scale production, numerical values of the conversion and selectivity given in the above-cited Patent Specifications and other publications should be subjected to suitable correction depending on the method of preparing the catalyst.

As a result of research conducted to eliminate the aforesaid defects of the conventional catalysts, the present inventors have found that a catalyst comprising Mo, P, Zr, V, Mn, X, and O (where X is at least one member selected from the group consisting of K, Rb, Cs, and Tl) in a specific ratio is a high-performance catalyst which can produce methacrylic acid in a very high selectivity, can inhibit the formation of carbon mono- and dioxides at a low level; and is easy in reaction control, and simultaneously has an improved mechanical strength owing to an increase in adhesion of the catalyst active component particles to one another and, hence, is desirable for use in the commercial scale production.

An object of this invention is to provide a catalyst for producing methacrylic acid with a high selectivity.

Another object of this invention is to provide a catalyst for oxidizing acrolein, which has sufficient physical strength to endure severe conditions for use on a commercial scale.

A further object of this invention is to provide a process for producing methacrylic acid by oxidizing methacrolein with a high selectivity by use of the above-said catalyst.

Other objects and advantages of this invention will become apparent from the following description.

According to this invention, there is provided a process for producing methacrylic acid from methacrolein by gas-phase catalytic oxidation, which comprises subjecting to reaction methacrolein, a molecular oxygen-containing gas and steam in a molar ratio of methacrolein:molecular oxygen:steam of 1:1–3:0–50 at a temperature in the range of 250° to 400° C. at a space velocity of 250 to 3,000 hr$^{-1}$ (at 0° C. and 1 atm.) in the presence of a catalyst having the composition formula, $$Mo_a P_b Zr_c V_d Mn_e X_f O_g$$

wherein X represents at least one member selected from the group consisting of K, Rb, Cs, and Tl, and a, b, c, d, e, f, or g represents the number of atoms of Mo, P, Zr, V, Mn, X, or O, respectively, and when a=12, b=0.5–5, preferably 1–2, c=0.1–5, preferably 0.5–2, d=0.05–3, preferably 0.1–1, e=0.05–1.5, preferably 0.1–1, and f=0.1–3, preferably 1–2.5 and g=40–60, preferably 40–50, and g is the number of oxygen atoms sufficient to satisfy the valencies of the respective catalyst component elements.

When the number of atoms of each element constituting the catalyst is outside the above-mentioned range, the effect aimed at by this invention cannot sufficiently be obtained. In particular, when the number of atoms of Mn (e) is less than 0.05, the physical strength of the catalyst is not sufficient, and when it is more than 1.5, the activity of the catalyst is rather lowered. The number of atoms of Mn is preferably 0.1 to 1.

The catalyst used in the process of this invention is greatly excellent in selectivity for methacrylic acid and yield of methacrylic acid even when used in the form of a molded catalyst as obtained by tabletting. This is because the present catalyst can be molded by tabletting under a moderate pressure. It is also possible to obtain a supported catalyst having a sufficiently high physical strength and satisfactory performance characteristics by adhering the present catalyst active component in the powder form to a commercially available molded carrier using a suitable medium.

One of the features common to the catalysts of the phosphorus-molybdenum-alkali system is that the adhesion of the catalyst active component particles to one another and to a carrier is not so good. Therefore, when it is intended to prepare a molded catalyst by a tabletting method, a high tabletting pressure is necessary to increase the physical strength, so that the catalyst activity is decreased. The present invention relates to a process for oxidizing methacrolein with a catalyst having the characteristic feature that Mn is added as an essential component to a methacrolein-oxidizing catalyst consisting of Mo, P, Zr, V, and K, Rb, Cs or Tl. According to the inventors' experiment, the addition of components other than Mn often adversely affects the catalyst activity though it results in an increase of physical strength. The present inventors have surprisingly found that Mn is a constituent capable of increasing the catalyst activity and, at the same time, the physical strength. Since a catalyst for use in industry is required to have not only an ability to increase the yield of an intended product, but also physical strength sufficient to withstand the severe conditions under which the catalyst is used, the discovery mentioned above should be regarded as important.

Such an effect of manganese is not easily predictable from the prior art. Although not popular, catalyst systems containing manganese for use in oxidizing an unsaturated aldehyde are described in, for example, Japanese Patent Publication No. 14,205/74 (Plasdoc No. 33623 W); DT-OS 2,351,687; Japanese Patent Application Kokai (Laid-open) No. 4,418/73 (Plasdoc No. 58858 U), and No. 4,419/73 (Plasdoc No. 58859 U); DT-OS No. 2,305,404 and U.S. Pat. No. 3,840,595. In these patent publications, however, manganese is described only as one of the many components which can be added to a catalyst, and the effect of manganese on the activity of the catalyst system is small. Said publications are quite silent on the remarkable effect of manganese on the improvement of physical strength for use as a practical catalyst. Since it is a common understanding by those skilled in the art that the effect of addition of a certain component is varied depending upon the kind of basic components, a beneficial effect of manganese on physical strength of a certain catalyst is unpredictable even if such an effect has been found on another catalyst system. The basic systems of catalyst disclosed in the above-cited patent publications are as follows: Mo - Sn system in Japanese Patent Publication No. 14,205/74 (Plasdoc No. 33623 V), Mo-Nb-Si system in DT-OS 2,351,687, Ge-Mo system in Japanese Patent Application Kokai (laid-open) No. 4,418/73, Ge-Mo-As system in Japanese Patent Application Kokai (laid-open) No. 4,419/73, Mo-Sb system in DT-OS No. 2,305,404 and Mo-V-W-Sn system in U.S. Pat. No. 3,840,595. It can be understood, therefore, that the effect of manganese on the P-Mo-Zr-V-alkali system is not easily predictable.

The catalyst active component may be prepared by a conventional method such as evaporation to dryness. For example, the following method may be used: An aqueous solution of a manganese compound, for instance, manganese-(II) phosphate monobasic ($Mn(H_2PO_4)_2$), manganese nitrate, or the like, and an aqueous solution of a phosphorus compound, for instance, orthophosphoric acid, is added to an aqueous solution of an appropriate molybdenum compound, for instance, phospho-molybdic acid or ammonium molybdate, and a powder of a zirconium compound, for instance, zirconium dioxide, is then added, after which the resulting mixture is sufficiently stirred and aged, and an aqueous solution of a vanadium compound, for instance, ammonium metavanadate, phospho-vanado-molybdic acid or the like, and an aqueous solution of an alkali metal or thallium nitrate or hydroxide, is added to the resulting reaction mixture. The resulting mixture is sufficiently stirred, evaporated to dryness on a water bath, and then calcined to form the catalyst active component.

The compounds to be used as the starting material for each element are preferably water-soluble. However, as the zirconium compound, particularly preferable is finely divided zirconium dioxide. The starting materials for the elements include the following compounds:

Mo: Ammonium molybdate, phosphomolybdic acid, ammonium phosphomolybdate, phosphovanadomolybdic acid, potassium molybdate, etc.

P: Phosphomolybdic acid, ammonium phosphomolybdate, phosphovanadomolybdic acid, phosphoric acid (ortho-, meta-, poly-, or tripoly-), etc.

Zr: Zirconium dioxide, zirconium silicate ($ZrSiO_4$), zirconyl nitrate ($ZrO(NO_3)_2$), zirconyl chloride ($ZrOCl_2$), etc.

V: Ammonium vanadate, phosphovanadomolybdic acid, vanadium oxide, etc.

Mn: Manganese (II) phosphate monobasic, manganese-(II) nitrate, etc.

X: Nitrates, hydroxides and carbonates of K, Rb, Cs and Tl, etc.

The catalyst active component obtained by the above-mentioned method is ground and then tabletted or adhered onto a carrier to form a catalyst which can be used in industry.

The tabletting may be effected as follows: The calcined catalyst active component is ground by means of a ball mill and then mixed with several percent of a lubricant, such as graphite powder or the like, and the resulting mixture is fed to a tabletting machine for the preparation of a medicine. The tabletting pressure ranges from 20 kg/cm² to 2,000 kg/cm². However, in the case of a tabletting machine of the type that not the tabletting pressure but the amount of powder per tablet is controlled, the amount of powder per tablet is determined by testing the strength of resulting tablets. In the preparation of tablets, the strength of the tablets can be increased by imparting to the powder an appropriate moisture, but this way is not desirable because the catalyst activity is decreased thereby. However, in the case of the present catalyst system, the imparting of moisture is usually unnecessary.

The following is an example of adhering the catalyst active component to a carrier: The calcined catalyst active component is sufficiently ground by means of a ball mill to form a finely divided powder, and the powder and a spray of water or another appropriate low boiling solvent are alternately applied to a carrier having, preferably, a spherical shape and having a rough surface while being thoroughly stirred to gradually adhere the powder onto the carrier. As the carrier, there may be used carriers having a low surface area which are used in conventional oxidation reaction, such as molten alumina, silicon carbide, pumice or the like.

The catalyst active component prepared by the above-noted method is calcined in an air stream, ordinarily at 250° to 500° C., preferably 300° to 470° C., generally for 2 to 40 hours to form a catalyst ready for use.

The molecular-oxygen-containing gas used in the present process is air or a mixture of molecular oxygen with an inert gas such as, for example, nitrogen, carbon dioxide, helium, argon, or a lower saturated hydrocarbon.

The reaction conditions for carrying out the present process may be varied in a wide range depending on the catalyst composition, though are generally as follows:

(1) Reaction temperature: 250° to 400° C.
(2) Reaction pressure: 0.5 to 3 atmosphere absolute.
(3) Space velocity: 250–3,000 $hr^{-1}$ (at 0° C. and 1 atm.).
(4) Molar ratio of methacrolein to molecular oxygen: 1:1–3, preferably 1:1–2.
(5) Molar ratio of methacrolein to steam: 1:0–50, preferably 1:5–40.

The reaction products can be separated and recovered in an ordinary way such as, for example, condensation, extraction, and other techniques.

The invention is further illustrated below with reference to Examples which are merely illustrative and not limitative.

In Examples and Comparative Examples, analysis was conducted by a gas chromatography and conversion and selectivity were calculated by the following equations, and the mole percent thus obtained is simply expressed "%":

Conversion of methacrolein (mole %)
$$= \frac{\text{Supplied methacrolein (mole)} - \text{Unreacted methacrolein (mole)}}{\text{Supplied meth acrolein (mole)}} \times 100$$

Selectivity for methacrylic acid (mole %)
$$= \frac{\text{Formed methacrylic acid (mole)}}{\text{Supplied methacrolein (mole)} - \text{Unreacted methacrolein (mole)}} \times 100$$

Yield of methacrylic acid (mole %)
= (Conversion of methacrolein) × (selectivity for methacrylic acid) × $\frac{1}{100}$ Selectivity for acetic acid (mole %)
$$= \frac{\text{Formed acetic acid (mole)}}{\text{Supplied methacrolein (mole)} - \text{Unreacted methacrolein (mole)}} \times 50$$

Selectivity for carbon monoxide and carbon dioxide (mole %)
$$= \frac{\text{Formed } CO_2 \text{ and CO (mole)}}{\text{Supplied methacrolein (mole)} - \text{Unreacted methacrolein (mole)}} \times 25$$

EXAMPLE 1

An aqueous solution of 57.0 g (15.6 millimoles) of phosphomolybdic acid was prepared in a 1-liter beaker. An aqueous solution of 0.86 g (3.90 millimoles) of manganese (II) phosphate monobasic and 0.90 g of 85% orthophosphoric acid (7.81 millimoles of orthophosphoric acid) was separately prepared and added to the above solution, and the resulting solution was thoroughly stirred. To the resulting solution was added 3.86 g (31.25 millimoles) of powdered zirconium dioxide. The mixture was heated with stirring in a water bath at 60° C. for 48 hours and then allowed to stand for cooling. To the cooled mixture was added an aqueous solution of 0.91 g (7.81 millimoles) of ammonium metavanadate, followed by adding an aqueous solution of 12.18 g (62.5 millimoles) of cesium nitrate, and the resulting mixture was thoroughly stirred. The resulting mixture was evaporated to dryness on a water bath. The dried mass was transferred to an evaporating dish and calcined in an air atmosphere in a muffle furnace at 400° C. for one hour, then at 450° C. for 2 hours. The calcined mass was ground in a mortar, admixed with 5% by weight of powdered graphite, thoroughly mixed, and formed by means of a tabletting machine into tablets, 6.5 mm in diameter and 3 mm in thickness, to prepare the catalyst. The atomic ratio of the constituents in the thus obtained catalyst was Mo:P:Zr:V:Cs:Mn=12:1.5:1:0.25:2:0.125.

A heat-resisting glass tube reactor, 20 mm in inner diameter, was packed with 25 cc of the above catalyst. A gaseous mixture comprising methacrolein, air, and steam in a molar ratio of 4.6:35.0:60.4 was passed through the catalyst layer at a reaction temperature of 340° C. at a space velocity of 1,000 $hr^{-1}$. The data obtained after 3 to 4 hours from the beginning of reaction were as shown in Table 1.

Falling resistance was tested by allowing the catalyst to fall from the top of a vertical glass tube, 2.5 m in length and 20 mm in inner diameter, to which an impact-resistant flask was attached at the bottom. No change was observed, except that about 3% of the test tablets showed chipping at the edge.

COMPARATIVE EXAMPLE 1

A catalyst was prepared in the same manner as in Example 1, except that no manganese compound was added. The reaction was carried out also in the same manner as in Example 1. The results obtained were as shown in Table 1.

Table 1 shows that when manganese is added to the catalyst, selectivity for methacrylic acid increases while selectivity for carbon mono- and dioxides decreases from 15.5% to 11.2%, the difference being 4.3%. Such a decrease in selectivity for carbon mono- and dioxides indicates that the heat generated in the reactor is diminished, resulting in an easy control of the reaction.

Falling resistance of the catalyst obtained above was tested in the same way as in Example 1. About 15% of the test tablets showed more or less chipping at the edge and about one-third of the chipped tablets showed considerable damage.

EXAMPLES 2 TO 7 AND COMPARATIVE EXAMPLES 2 TO 5

A number of catalysts were prepared in the same manner as in Example 1, except that the manganese content and the kind of X were varied. Oxidation reaction of methacrolein was carried out in the same manner under the same conditions as in Example 1. In Example 3, a combination of manganese (II) phosphate monobasic and manganese nitrate was used. Compounds used to supply X were potassium hydroxide, cesium nitrate, rubidium nitrate, and thallium nitrate. The results obtained were as shown in Table 1.

EXAMPLE 8

An aqueous solution of 45.1 g (12.35 millimoles) of phosphomolybdic acid and 14.1 g (7.8 millimoles) of phosphovanadomolybdic acid was prepared in a 1-liter beaker. 3.86 Grams (31.2 millimoles) of powdered zirconium dioxide was added to the above solution, heated with stirring for 48 hours in a water bath at 60° C., and then allowed to stand for cooling. To the resulting mixture was added with thorough stirring an aqueous solution of 7.30 g (37.44 millimoles) of cesium nitrate, 1.75 g (31.2 millimoles) of potassium hydroxide, and 2.24 g (7.8 millimoles) of manganese nitrate, followed by adding thereto an aqueous solution of 1.80 g of 85% (weight) ortho-phosphoric acid (15.6 millimoles of ortho-phosphoric acid). The resulting mixture was evaporated to dryness on a water bath, then transferred to an evaporating dish, and calcined in an air atmosphere in a muffle furnace at 400° C. for one hour, then at 450° C. for 2 hours. The calcined mass was thoroughly ground in a mortar.

A commercially available α-alumina carrier (4AS01 of Fujimi Kenmazai Co.), 3 mm in particle size, was sprayed with a little water, followed by dusting the powdered catalyst active component obtained above. The spraying and dusting treatments were repeated until 45 g of the powdered catalyst active component had been supported on 30 g of the carrier and the particle size had become 4.0 to 4.2 mm. The supported catalyst was calcined in a muffle furnace at 400° C. for 3 hours and used in the reaction. The atomic ratio of the active constituents in the supported catalyst was Mo:P:Zr:V:Cs:K:Mn = 12:1.54:1:0.5:1.2:1:0.25.

The reaction was carried out in the same manner as in Example 1. The conversion was 90.1%, and the selectivity was 75.3% for methacrylic acid, 8.1% for acetic acid, 10.1% for carbon oxides, and the yield of methacrylic acid was 67.8%.

The physical strength of the supported catalyst was tested in the same way as in Example 1. No disintegration was observed. On repeating the test on the supported catalyst which had already undergone the test, no change was observed, except that about 20% of the supported catalyst showed partial peeling-off of the catalyst.

COMPARATIVE EXAMPLE 6

A supported catalyst was prepared in the same manner as in Example 8, except that no manganese nitrate was added. The atomic ratio of the active constituents in the supported catalyst was Mo:P:Zr:V:Cs:K = 12:1.54:1:0.5:1.2:1.

The reaction was carried out in the same manner as in Example 1. The conversion was 75.1%, the selectivity was 70.0% for methacrylic acid, 8.0% for acetic acid, 11.1% for carbon oxides, and the yield of methacrylic acid was 52.6%.

The physical strength of the supported catalyst was tested in the same way as in Example 1. No disintegration was observed. On repeating the test on the supported catalyst which had already undergone the test, about 50% of the supported catalyst showed partial peeling-off of the catalyst.

From the above results, it was found that the supported catalyst obtained in the present Comparative Example was inferior to that obtained in Example 8 in physical strength and catalyst activity.

COMPARATIVE EXAMPLE 7

An aqueous solution was prepared by dissolving 23.4 g of ammonium meta-vanadate in warm water containing 35.1 g of oxalic acid. This solution was added with stirring to an aqueous solution prepared by dissolving with moderate heating 212 g of ammonium molybdate in distilled water. To the resulting solution were added an aqueous solution of 23 g of 85% orthophosphoric acid and an aqueous solution of 39.0 g of cesium nitrate. The resulting mixture, while being stirred, was evaporated to dryness. The resulting composition was calcined in a muffle furnace at 400° C. for 3 hours, then crushed coarsely, and seived to collect the particles, 4 to 8 mesh in size, which were used as a catalyst. The atomic ratio of this catalyst was Mo:P:V:Cs = 12:2:1:2. Methacrolein was oxidized with this catalyst in a manner similar to that in Example 1. The conversion of methacrolein was 86.3%, the selectivity was 70.5% for methacrylic acid, 8.5% for acetic acid, 12.1% for carbon oxides, and the yield of methacrylic acid was 60.8%.

COMPARATIVE EXAMPLE 8

The catalyst particles of the sizes other than 4 to 8 mesh, which were obtained in Comparative Example 7 and not used as catalyst, were ground in a ball mill. The resulting powder was supported on an α-alumina carrier (4AS01 of Fujimi Kenmazai Co.), 3 mm in particle diameter. The particles obtained by supporting 45 g of said powder on 30 g of α-alumina carrier were calcined in a muffle furnace at 400° C. for 3 hours to prepare a supported catalyst.

Methacrolein was oxidized with the above supported catalyst in the same manner as in Comparative Example 7. The conversion of methacrolein was 83.5%, selectivity was 68.5% for methacrylic acid, 11.0% for acetic acid, and 16.5% for carbon oxides, and the yield of methacrylic acid was 57.2%.

The supported catalyst was tested for physical strength in the same way as in Example 1. On the first testing, 85% of the catalyst showed partial peeling-off. It was thus found that the catalyst having this composition used in Comparative Example 7 was very weak.

COMPARATIVE EXAMPLE 9

A supported catalyst was prepared in the same manner as in Comparative Example 8, except that zirconium oxide was additionally incorporated in the catalyst composition. Methacrolein was oxidized with this catalyst in the same manner as in Comparative Example 8. The conversion of methacrolein was 88.5%, the selectivity was 72.1% for methacrylic acid, 7.5% for acetic acid, and 12.0% for carbon oxides, and the yield of methacrylic acid was 63.8%.

The above supported catalyst was tested for physical strength in the same way as in Example 1. On the first testing, about 75% of the catalyst showed partial peeling-off.

By comparing the results obtained in Comparative Example 8 with those obtained in Comparative Example 9, zirconium was found to be effective in increasing both the selectivity for methacrylic acid and the physical strength of the catalyst. However, the improvement is still insufficient for the catalyst to be used in a practical operation.

EXAMPLE 9

A supported catalyst was prepared in the same manner as in Comparative Example 9, except that manganese nitrate was additionally incorporated in preparing the catalyst. Methacrolein was oxidized with the above supported catalyst in the same manner as in Comparative Example 9. The conversion of methacrolein was 88.7%, selectivity was 78.5% for methacrylic acid, 7.4% for acetic acid, and 10.1% for carbon oxides, and the yield of methacrylic acid was 69.6%.

The above supported catalyst was tested for the physical strength in the same way as in Example 1. On the first testing, no disintegration was observed. On repeating the testing on the supported catalyst which had already undergone the testing, about 20% of the supported catalyst showed partial peeling-off.

By comparing the above results with those obtained in Comparative Example 9, it is seen that the addition of manganese improves the selectivity for methacrylic acid and markedly improves the physical strength of the catalyst.

ity of 250 to 3,000 hr$^{-1}$ (at 0° C. and 1 atm.) with a catalyst having the following composition formula in atomic ratio:

$$Mo_aP_bZr_cV_dMn_eX_fO_g$$

wherein X represents at least one member selected from the group consisting of potassium, rubidium, cesium, and thallium, and a, b, c, d, e, f or g represents the number of atoms of Mo, P, Zr, V, Mn, X or O, respectively, and a is 12, b is 0.5 to 5, c is 0.1 to 5, d is 0.05 to 3, e is 0.05 to 1.5, f is 0.1 to 3 and g is 40 to 60, and g is a number sufficient enough to satisfy the valencies of the respective catalyst component elements.

2. A process according to claim 1, wherein the value of e is 0.1 to 1.

3. A process according to claim 2, wherein b is 1–2, c is 0.5–2, d is 0.1–1, f is 1–2.5 and g is 40–50.

4. A process according to claim 1, wherein the molecular oxygen-containing gas is air or a mixture of molecular oxygen with an inert gas.

5. A process according to claim 4, wherein the inert gas is nitrogen, carbon dioxide, helium, argon, or a lower saturated hydrocarbon.

6. A process according to claim 1, wherein the molar ratio of methacrolein to steam is 1:5–40.

Table 1

| | Catalyst Composition | | | | | | Composition (%) | Selectivity (%) | | | Yield of methacrylic acid (%) |
|---|---|---|---|---|---|---|---|---|---|---|---|
| | Mo | P | Zr | V | X | Mn | | Methacrylic acid | Acetic acid | Carbon monoxide and carbon dioxide | |
| Example 1 | 12 | 1.5 | 1 | 0.25 | Cs 2 | 0.125 | 90.0 | 75.1 | 7.5 | 11.2 | 67.6 |
| Comp. Ex. 2 | 12 | 1.5 | 1 | 0.25 | Cs 2 | — | 90.3 | 69.4 | 7.8 | 15.5 | 62.7 |
| Example 2 | 12 | 1.5 | 1 | 0.25 | Cs 2 | 0.25 | 87.8 | 76.5 | 7.4 | 10.5 | 67.2 |
| Example 3 | 12 | 1.5 | 1 | 0.25 | Cs 2 | 1 | 69.8 | 77.5 | 7.4 | 10.5 | 54.1 |
| Example 4 | 12 | 1.5 | 1 | 0.25 | Rb 2 | 0.25 | 80.1 | 79.3 | 6.5 | 12.4 | 63.5 |
| Comp. Ex. 2 | 12 | 1.5 | 1 | 0.25 | Rb 2 | — | 82.3 | 74.5 | 6.3 | 15.1 | 61.3 |
| Example 5 | 12 | 1.5 | 1 | 0.25 | K 2 | 0.25 | 76.5 | 85.1 | 5.3 | 7.0 | 65.1 |
| Comp. Ex. 3 | 12 | 1.5 | 1 | 0.25 | K 2 | — | 80.4 | 79.9 | 5.2 | 10.3 | 64.2 |
| Example 6 | 12 | 1.5 | 1 | 0.25 | Tl 2 | 0.25 | 79.8 | 72.3 | 7.5 | 11.5 | 57.7 |
| Comp. Ex. 4 | 12 | 1.5 | 1 | 0.25 | Tl 2 | — | 83.1 | 68.5 | 7.5 | 15.5 | 56.9 |
| Example 7 | 12 | 1.5 | 1 | 0.25 | K 1.7 Cs 0.25 | 0.25 | 80.3 | 84.5 | 6.5 | 7.7 | 67.9 |
| Comp. Ex. 5 | 12 | 1.5 | 1 | 0.25 | K 1.7 Cs 0.25 | — | 84.2 | 80.3 | 5.2 | 11.0 | 67.6 |
| Example 8 | 12 | 1.54 | 1 | 0.5 | K 1 Cs 1.2 | 0.25 | 90.1 | 75.3 | 8.1 | 10.1 | 67.8 |
| Comp. Ex. 6 | 12 | 1.54 | 1 | 0.5 | K 1 Cs 1.2 | — | 75.1 | 70.0 | 8.0 | 11.1 | 52.6 |
| Example 9 | 12 | 2 | 1 | 1 | Cs 2 | 0.5 | 88.7 | 78.5 | 7.4 | 10.1 | 69.6 |
| Comp. Ex. 7 | 12 | 2 | — | 1 | Cs 2 | — | 86.3 | 70.5 | 8.5 | 12.1 | 60.8 |
| Comp. Ex. 8 | 12 | 2 | — | 1 | Cs 2 | — | 83.5 | 66.5 | 11.0 | 16.5 | 57.2 |
| Comp. Ex. 9 | 12 | 2 | 1 | 1 | Cs 2 | — | 88.5 | 72.1 | 7.5 | 12.0 | 63.8 |

What is claimed is:

1. A process for producing methacrylic acid from methacrolein by gas-phase oxidation, which comprises subjecting to reaction methacrolein, a molecular oxygen-containing gas and steam in a molar ratio of methacrolein:molecular oxygen:steam of 1:1–3:0–50 at a temperature in the range of 250° to 400° C. at a space veloc- 7. A process according to claim 6, wherein the molar ratio of methacrolein to molecular oxygen is 1:2.

8. A process according to claim 1, wherein the molar ratio of methacrolein to molecular oxygen is 1:1–2.

9. A process according to claim 1, wherein the reaction pressure is 0.5 to 3 atmosphere absolute.

* * * * *